(12) United States Patent
Nike

(10) Patent No.: US 8,353,702 B1
(45) Date of Patent: Jan. 15, 2013

(54) DENTAL IMPLANT SYSTEM

(75) Inventor: Leo Nike, Mississauga (CA)

(73) Assignee: Adaptall Manufacturing Inc., Mississauga (CA)

( * ) Notice: Subject to any disclaimer, the term of this patent is extended or adjusted under 35 U.S.C. 154(b) by 0 days.

(21) Appl. No.: 13/348,755

(22) Filed: Jan. 12, 2012

(51) Int. Cl.
*A61C 8/00* (2006.01)

(52) U.S. Cl. ....................................... 433/173

(58) Field of Classification Search ........... 433/172–176
See application file for complete search history.

(56) References Cited

U.S. PATENT DOCUMENTS

| | | |
|---|---|---|
| 3,576,074 A | 4/1971 | Gault |
| 3,934,347 A | 1/1976 | Lash et al. |
| 4,178,686 A | 12/1979 | Riess et al. |
| 4,293,302 A | 10/1981 | Hassler et al. |
| 4,411,624 A | 10/1983 | Ogino et al. |
| 4,497,629 A | 2/1985 | Ogino et al. |
| 5,197,881 A | 3/1993 | Chalifoux |
| 5,312,253 A | 5/1994 | Chalifoux |
| 5,437,551 A | 8/1995 | Chalifoux |
| 5,509,804 A | 4/1996 | Arzt |
| 5,954,505 A | 9/1999 | Ford |
| 6,273,720 B1 | 8/2001 | Spalten |
| 2004/0259056 A1 | 12/2004 | Holt |
| 2008/0261176 A1 * | 10/2008 | Hurson ........................ 433/174 |
| 2009/0061385 A1 | 3/2009 | Bahcall et al. |
| 2010/0203475 A1 | 8/2010 | Yoon et al. |

* cited by examiner

*Primary Examiner* — Cris L Rodriguez
*Assistant Examiner* — Eric Rosen
(74) *Attorney, Agent, or Firm* — Richies, McKenzie & Herbert LLP

(57) ABSTRACT

A dental implant system is described which includes a root form for attaching to a patient's jaw bone and an abutment. The root form has a cavity. Furthermore, the abutment has an attachment portion, an insertion portion and an aperture. The insertion portion may be receivable within the cavity and form a taper lock therein. Finally, the aperture may pass through the abutment from the attachment portion to the insertion portion. In a preferred embodiment, the aperture is configured to receive a predetermined amount of hydraulic pressure to eject the abutment from the cavity, whereby the predetermined amount of hydraulic pressure overcomes the taper lock between the insertion portion of the abutment and the cavity.

18 Claims, 6 Drawing Sheets

DENTAL IMPLANT SYSTEM

FIELD OF THE INVENTION

This invention relates to dental implants and, in particular, a multi-part dental implant system.

BACKGROUND OF THE INVENTION

Dental implant systems are well known in the art for replacing one or more dead or missing teeth. For example, common dental implant systems include a base which is integrated into one of the upper and lower jaw, and an abutment which attaches to the base. The base is often called a root form, as it looks and behaves similar to the root or roots of a tooth or teeth. Once the abutment is attached to the root form, a dental prosthesis is bonded to the abutment using known techniques. The dental prosthesis may take the form of a replacement tooth, a bridge and the like.

Installing a dental implant into a patient's mouth is often a multi-step process. For example, typical approaches to implantation may include preparing a site for implantation, surgically inserting a root form into the jaw, allowing a sufficient amount of time for the root form to osseointegrate (i.e. fuse with the surrounding bone), connecting an abutment to the root form, and finally attaching a replacement prosthesis to the abutment. A multi-step process involving a multi-part dental implant system is the preferred approach for many dentists and dental surgeons, as it allows for the proper integration of the root form within the surrounding bone (usually taking between 2 to 6 months) without the root form being affected by a patient's chewing during the osseointregration step. When suitably integrated into the jaw, the root form may provide a solid anchor in which to attach the abutment and subsequent dental prosthesis may be connected.

Typical dental implant technology often employs the use of threads to connect the abutment to the root form implanted within the jaw. For example, the dental implant may utilize corresponding threads on both the root form and the abutment to allow the abutment to be screwed into the root form. Once connected, the abutment may have an attachment connector or end for bonding a dental prosthesis to the abutment. The dental prosthesis may be glued, cemented or otherwise connected to the abutment.

While typical dental implants allow for the connection of a dental prosthesis to a root form, the inventors have appreciated that the diameter and pitch of different threaded abutments vary from one manufacturer to another.

Furthermore, where a patient with an installed dental implant is involved in a trauma, such as a motor vehicle accident or a sports-related injury, a portion of the abutment may break off or shear. The threads of the abutment and/or root form may also become damaged by other means. If this occurs, a dentist or dental surgeon may have difficulty in removing the abutment from the root form and finding a replacement abutment.

The inventors have also appreciated that, in some cases, damage to the threads of the root form and/or the abutment may make removal or replacement of the damaged abutment impossible. In other cases, the dentist and/or dental surgeon may be unable to identify or distinguish the threads of the root form in order to locate a replacement abutment even with known thread identification tools. In this situation, the dentist or dental surgeon may be forced to remove the osseointegrated root form and begin the multi-step implantation process over again by installing a new root form. If a new root form is required, a patient will require adequate time (often months) to recover from the removal of the previous root form before the new root form can be surgically installed. Even more time will then be required for the new root form to become osseointegrated and for a new abutment and dental prosthetic to be put in place. Accordingly, replacing an installed dental implant with a new root form is both time-consuming and uncomfortable for the patient.

SUMMARY OF THE INVENTION

Accordingly, it is an object of this invention to provide an improved dental implant system.

In one aspect, the present invention resides in a dental implant system including a root form for attaching to a patient's jaw bone and an abutment. The root form has a cavity. Furthermore, the abutment has an attachment portion, an insertion portion and an aperture. The insertion portion may be receivable within the cavity and form a taper lock therein. Finally, the aperture may pass through the abutment from the attachment portion to the insertion portion.

In a preferred embodiment, the aperture is configured to receive a predetermined amount of hydraulic pressure to eject the abutment from the cavity, whereby the predetermined amount of hydraulic pressure overcomes the taper lock between the insertion portion of the abutment and the cavity.

Advantageously, in at least one embodiment the present invention provides for a dental implant system that does not require the removal of an osseointegrated implant in the event that there is a catastrophic failure or an unforeseen traumatic event. Instead, the damaged abutment can be removed using hydraulic pressure and a new abutment can be readily installed with a new dental prosthesis.

In another aspect, the present invention resides in a method for replacing an abutment in a dental implant system. The method includes the steps of preparing the abutment for removal from a cavity of a root form; inserting a medium into an aperture of the abutment; increasing the hydraulic pressure within the aperture; removing the abutment from the cavity when the hydraulic pressure reaches a predetermined amount of hydraulic pressure; and installing a replacement abutment into the root form. When preparing the abutment for removal, the abutment may form a taper lock within the cavity. Furthermore, when increasing the hydraulic pressure within the aperture, the aperture may lead to a contact surface between the abutment and the cavity.

In respect to post surgical trauma where the abutment is sheared off, the present invention offers a clinician (i.e. a dentist or a dental surgeon) an alternative method to the surgical removal of the implant. Access to the aperture is all that is required to facilitate the removal of the damaged abutment with the aid of hydraulics.

Further and other features of the invention will be apparent to those skilled in the art from the following detailed description of the embodiments thereof.

BRIEF DESCRIPTION OF THE DRAWINGS

Reference may now be had to the following detailed description taken together with the accompanying drawings in which.

DETAILED DESCRIPTION OF THE PREFERRED EMBODIMENTS

Figure 1A:
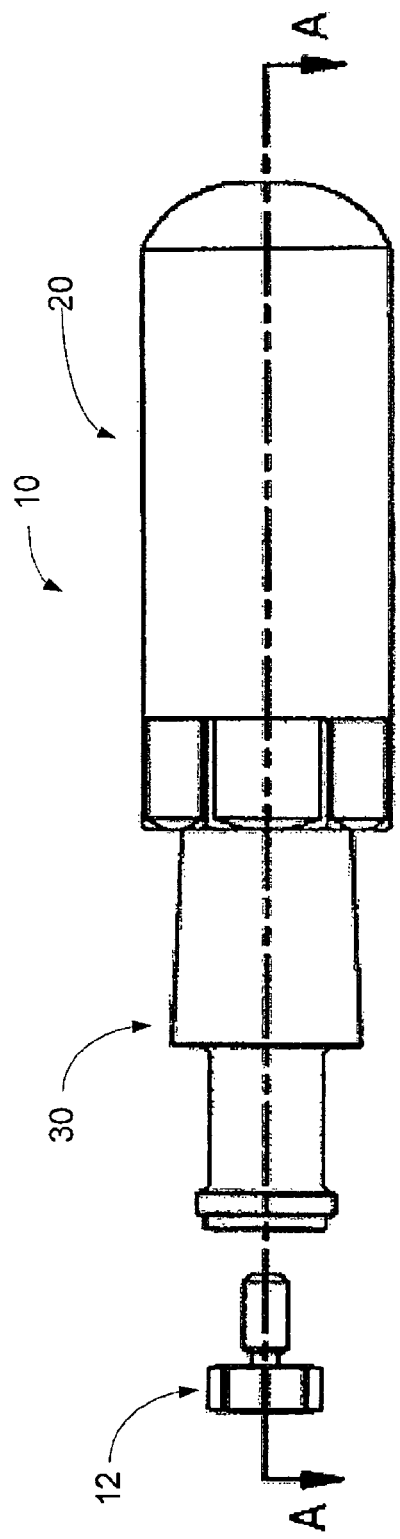
FIG. 1A shows a front elevation view of a dental implant system ha accordance with an embodiment of the present invention.
Figure 1B:
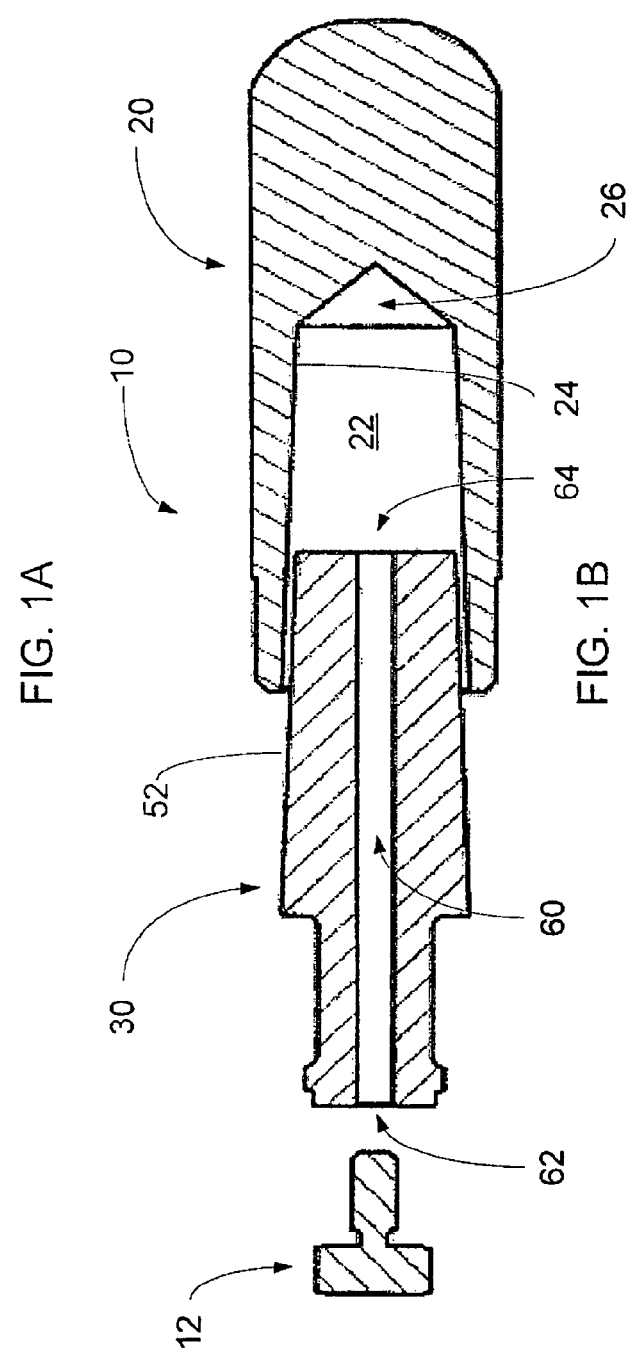
FIG. 1B shows a cross-section view of the dental implant system shown in FIG. 1A along line A-A.

As illustrated in FIG. 1A, FIG. 1B, FIG. 2A, FIG. 2B, FIG. 3 and FIG. 4, a dental implant system 10 is shown hi accordance with embodiments of the present invention. The dental implant system 10 includes a root form 20 and an abutment 30. The abutment 30 is receivable within the cavity 22. For example, as seen in FIG. 1B, the abutment 30 is slideably received within the root form 20 and forms a taper lock (i.e. friction fit) within a cavity 22 of the root form 20, once fully inserted.

Figure 2A:
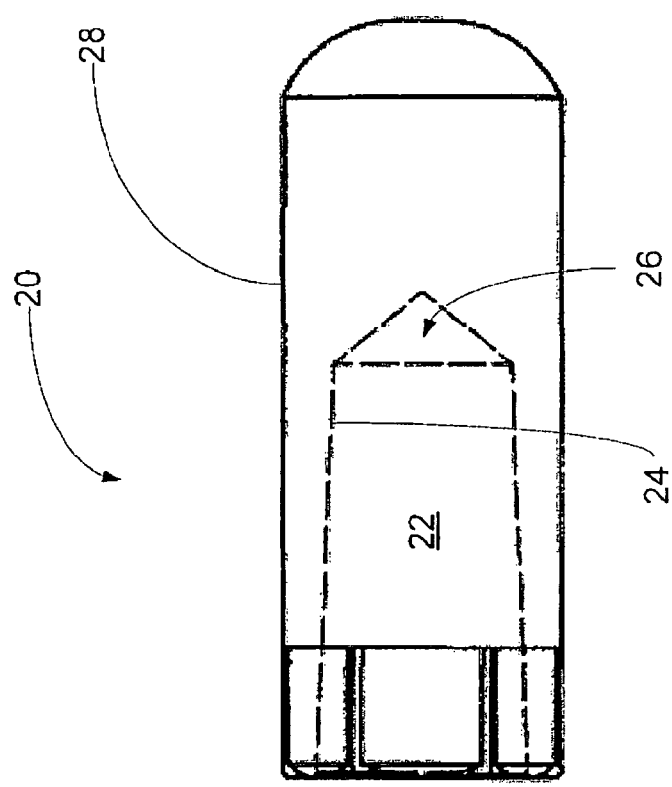
FIG. 2A shows a front elevation view of a root form hi accordance with an embodiment of the present invention.

As seen in FIG. 2A, the root form 20 includes the cavity 22 having a cavity sidewall 24. The cavity sidewall 24 of the cavity 22 is tapered for slideably receiving the abutment 30. As shown in FIG. 2A, the cavity 22 may be frustoconical or have at least a frustoconical portion. However, it should be understood that other shapes for the cavity 22 are also possible.

The cavity 22 may also have a chamber 26 disposed within the cavity 22. The chamber 26 may be disposed at the inner end of the cavity 22. When the abutment 30 is received within the cavity 22, the chamber 26 is not displaced or filled by the abutment 30, but rather provides a volume or space between the end of the abutment 30 and the cavity 22. Accordingly, the chamber 26 may be filled with a liquid and/or gas (not shown) when the abutment 30 is received within the cavity 22.

As seen in FIG. 2A, the chamber 26 is conical. The shape of the chamber 26 may be configured to distribute any increase in hydraulic pressure evenly along a cavity sidewall 24 of the cavity 22. However, it should be understood that other shapes for the chamber are also possible. For example, the chamber 26 may be rounded. In other embodiments, the chamber 26 may be frustoconical and may consist of an extension of the cavity 22 that remains free of the abutment 30 once the abutment has been received within the cavity 22.

An exterior 28 of the root form 20 may take a shape and/or texture common to dental implants known in the art. For example, the exterior 28 of the root form 20 may be ribbed or textured to increase its surface area and to improve osseointegration when surgically implanted within a patient's jaw. Furthermore, the root form 20 may be made of a suitable biocompatible material such as, for example, medical-grade titanium and the like.

Figure 2B:
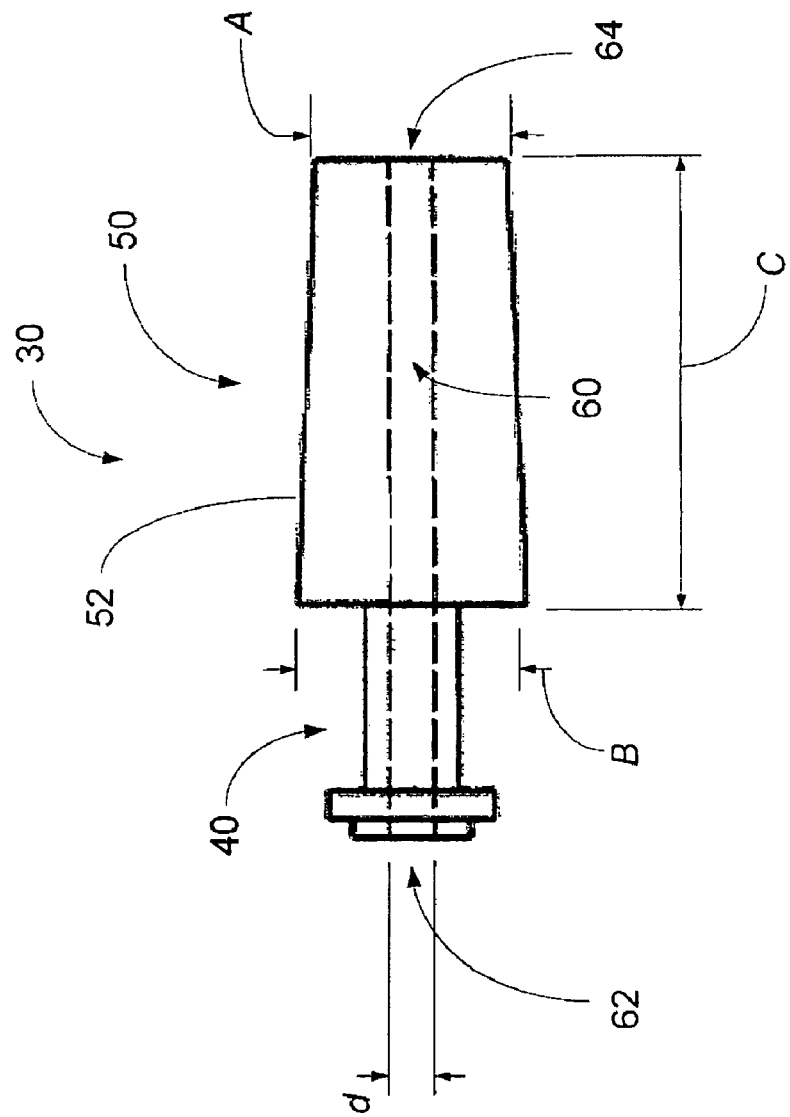
FIG. 2B shows a from elevation view of an abutment in accordance with an embodiment of the present invention.
Figure 3:
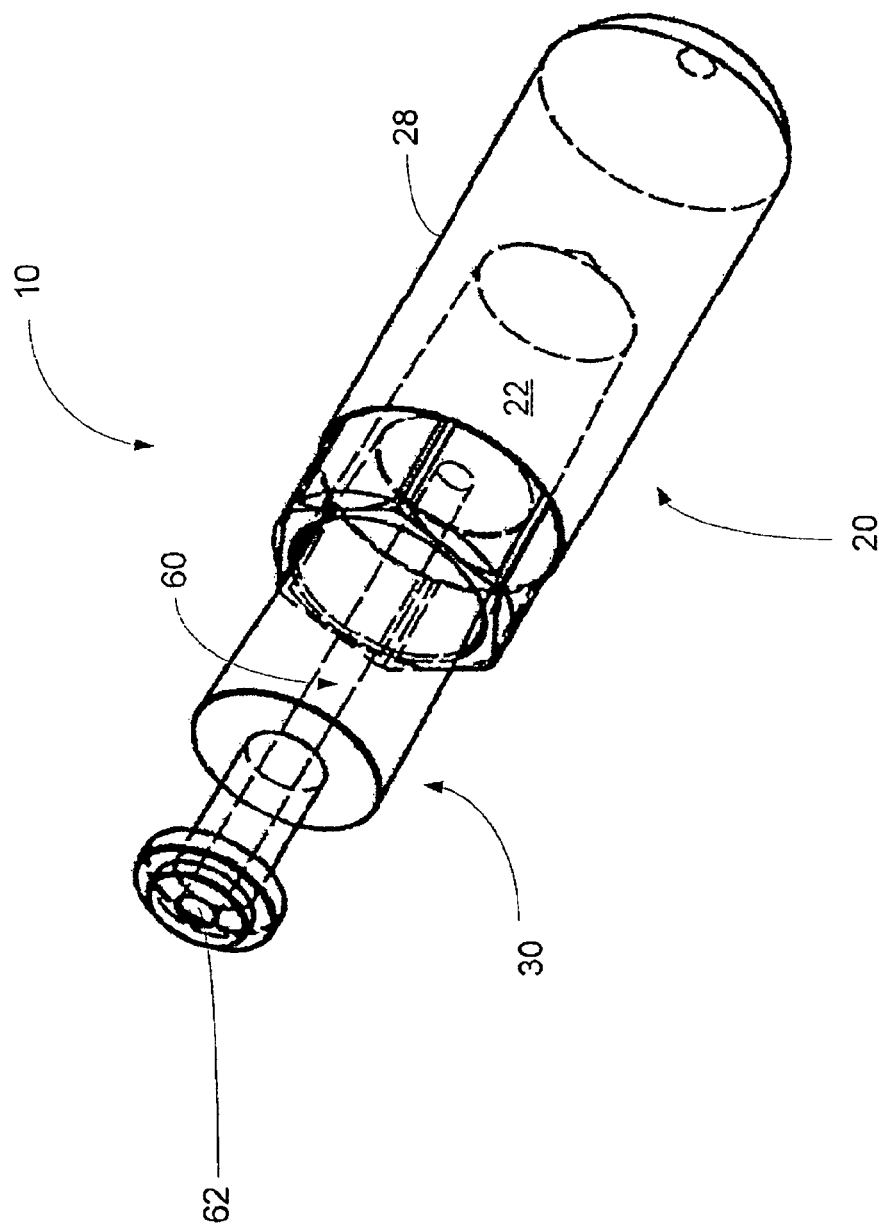
FIG. 3 shows a perspective view of a dental implant system in accordance with an embodiment of the present invention.
Figure 4:
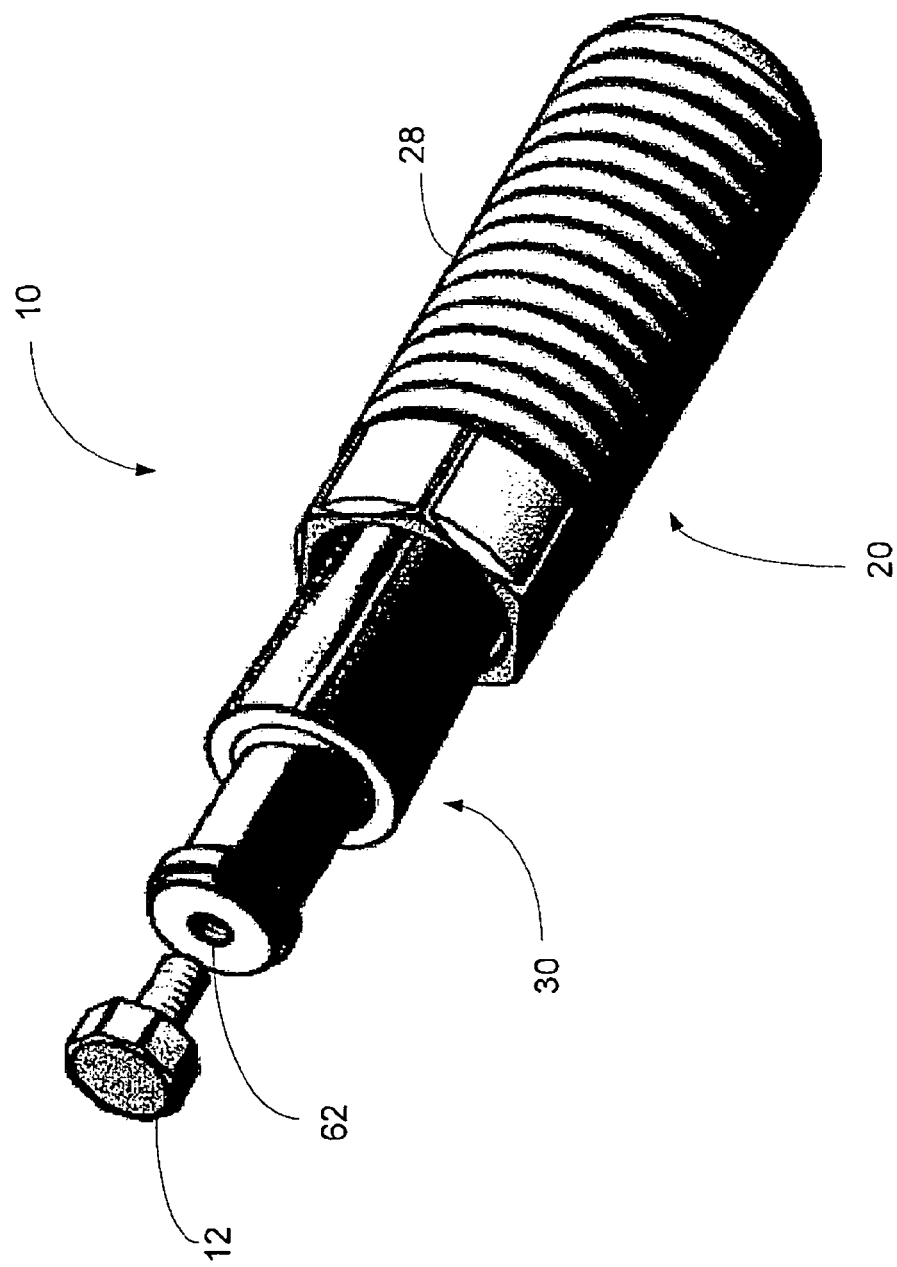
FIG. 4 shows a perspective view of a dental implant system in accordance with another embodiment of the present invention.

As seen in FIG. 2B, the abutment 30 includes an attachment portion 40 and an insertion portion 50. The attachment portion 40 of the abutment 30 is coupled to the insertion portion 50. For example, in some embodiments the attachment portion 40 and the insertion portion 50 may be attached by a weld, an adhesive and the like. In other embodiments, the attachment portion 40 and the insertion portion 50 may be integrally formed. For example, the abutment 30 may be milled, pressed or blanked out of a single piece of biocompatible material. In a preferred embodiment, the abutment 30 may be integrally formed out a single piece of titanium, such as medical-grade titanium.

The insertion portion 50 is configured to be received by the cavity 22 of the root form 20. For example, the shape of the insertion portion 50 may have an abutment wall 52 which is frustoconical. Furthermore, the shape of the insertion portion 50 may correspond to the shape of the cavity 22 of the root form 20 to form a taper lock or friction fit. In this manner, the abutment wall 52 of the insertion portion 50 may be tapered in a manner which mates with the cavity sidewall 24 of the root form 20. When the insertion portion 50 is received by the cavity 22, the abutment sidewall 52 and the cavity sidewall 24 are in contact to form a taper lock. For example, the insertion portion 50 may have dimensions slightly larger than the cavity 22 to provide the taper lock. In addition, the insertion portion 50 and the cavity 22 may be configured to provide uniform contact and/or pressure along the contact surface defined by the abutment sidewall 52 and the cavity sidewall 24.

A taper lock is also beneficial because it allows the abutment 30 to be received by the root form 20 in any orientation and/or direction. For example, as the insertion portion 50 and the cavity 22 are symmetric, the abutment 30 may be received within the root form 20 in any radial orientation on a 360 degree plane about its radius. Furthermore, even once received within the root form 20, the abutment 30 may be later repositioned in a different orientation by removing the abutment 30 from the cavity 22 and rotating the abutment 30 prior to reinsertion. In prior art embodiments where a prior art abutment is screwed into a prior art root form, the prior art abutment must be configured with a final resting position in mind. This final resting position must be predetermined prior to constructing the prior art abutment and root form, as the threads on the prior art abutment and cavity must be properly aligned.

The abutment 30 also includes an aperture 60 passing through the length of the abutment 30. The aperture 60 passes through the abutment 30 from the attachment portion 40 to the insertion portion 50. The aperture 60 includes an attachment opening 62 disposed towards the attachment portion 40 and an insertion opening 64 disposed towards the insertion portion 50. In some embodiments, the aperture 60 is cylindrical and has a diameter d. However, it should be understood that other shapes are also possible.

The attachment portion 40 of the abutment 30 is configured to connect a dental prosthesis (not shown) to the dental implant system 10. The dental prosthesis may be bonded or coupled to the attachment portion 40 using known techniques. For example, the dental prosthesis may be glued or cemented to the attachment portion 40.

Referring briefly to FIG. 1A, a prosthetic fastener 12 may be used to couple to the dental prosthesis to the abutment 30. In at least one embodiment, the prosthetic fastener 12 may be coupled to the attachment opening 62 of the aperture 60. For example, the prosthetic fastener 12 may be screwed into the attachment opening 62, such as shown briefly in FIG. 4.

In operation, the taper lock or friction fit formed between the cavity 22 of the root form 20 and the insertion portion 50 of the abutment 30 may be configured to provide a permanent (or semi-permanent) connection between the insertion portion 50 and the cavity 22. As seen in FIG. 1B, the insertion portion 50 and the cavity 22 include threadless tapers that slideably mate to form part of the dental implant system 10.

As appreciated by the inventors, the shape of the cavity 22 and the insertion portion 50 can be designed such that the resultant taper lock is operable to withstand separation pressures (or forces) from most day-to-day activities. For example, the taper lock is configured to provide a suitable connection such that the dental prosthesis (i.e. replacement tooth or teeth) may be used to bite into an apple or chew something hard and/or sticky.

However, the inventors have also appreciated that it may become necessary to remove the abutment 30 from the root form 20. For example, in a trauma or a sports-related event, the dental prosthesis may become damaged or sheared off. If such an event occurs, it may be necessary to replace the abutment 30 with a replacement abutment and new dental prosthesis. Accordingly, the threadless taper lock may be configured to require a predetermined amount of pressure or force to separate the insertion portion 50 from the cavity 22 once the taper lock is formed. This predetermined amount of pressure may be chosen to be greater than the pressures or forces typically experienced by a dental prosthetic within a patient's mouth. Accordingly, a proper balance must be achieved in which the taper lock is configured with sufficient strength to provide a sufficiently stable connection, while being separable when placed under a predetermined amount of pressure which is both controllable and which does not damage the root form or surrounding tissue and/or jaw.

Based on experimental results, the inventors have appreciated that the amount of pressure required to separate the taper lock from the insertion portion 50 and the cavity 22 may be a function of numerous factors. For example, the amount of pressure may be dependent upon the contact surface area, the total allowance, ultimate pressure required for assembly and the pressure factor of the insertion portion 50 and/or the cavity 22. In some embodiments, a basic equation relating the different factors may be expressed using the following equation:

$$P = \frac{A \times a \times F}{2}$$

As seen above, the ultimate pressure P required may be proportional to the contact area A between the abutment sidewall 52 of the insertion portion 50 and the cavity sidewall 24 of the cavity 22, the total allowance between the two surfaces, and the pressure factor F (based on the assumption that the diameter of the taper is twice the diameter of the bore).

Furthermore, the inventors have also appreciated that the slighter the taper, the greater the pressure required to separate the taper lock once formed between the insertion portion 50 and the cavity 22. This amount of pressure correlates to the ratio of taper R (i.e. decrease in diameter per unit length) which be expressed using the following equation:

$$R = \frac{\Delta D}{l} = \frac{B - A}{C}$$

As seen above, the taper ratio R is governed by the change in diameter D over the length of the taper l and can be further defined by a large diameter B, a small diameter A, and a length C of the frustoconical insertion portion 50 and/or the cavity 22.

Other factors governing the amount of pressure required to separate the insertion portion 50 from the cavity 22 may include: the taper ratio R, the finish on the cavity sidewall 24 and the abutment sidewall 52, and the surface area contacted between the cavity sidewall 24 and the abutment sidewall 52. For example, the inventors have appreciated that a smoother finish on the abutment sidewall 52 and the cavity sidewall 24 reduces the amount of pressure required to separate the insertion portion 50 from the cavity 22.

The shape of the chamber 26 may also aid in separating the abutment 30 from the root form 20. For example, the shape of the chamber 26 may be configured to direct the pressure exiting the insertion opening 64 of the aperture 60 towards the abutment sidewall 52 and the cavity sidewall 24.

To remove the abutment 30 from the root form 20, once the insertion portion 50 has been received within the cavity 22, a predetermined amount of force or pressure is required. For example, a predetermined amount of force may be used to pull the abutment 30 out of the cavity 22. However, where the attachment portion 40 of the abutment 30 has been damaged, such as in a trauma or similar situation, a dentist or dental surgeon may not have access to a surface or portion of the abutment 30 in which to grab onto in order to exert the necessary predetermined amount of force or pressure to separate the insertion portion 50 from the cavity 22. For example, when a patient is involved in a trauma or a sports-related event, the attachment portion 40 of the abutment 30 may break off or shear.

In such a situation, the dental implant system 10 is configured such that the aperture 60 may be used to direct the predetermined amount of pressure into the dental implant system 10 necessary to eject the abutment 30 from the root form 20. In a preferred embodiment, the predetermined amount of pressure may be directed into the attachment opening 62 and down the aperture 60. Furthermore, the predetermined amount of pressure may exit the aperture 60 at the insertion opening 64 and build up within the chamber 26 of the cavity 22. The build-up of pressure within the chamber 26 may then force the abutment 30 out of the cavity 22. In this manner, the predetermined amount of pressure is operable to overcome the taper lock created between the abutment sidewall 52 of the insertion portion 50 and the cavity sidewall 24 of the cavity 22 and eject the abutment 30 from the root form 20 without damaging either the cavity 22 or the root form 20. The abutment 30 is then separated from the root form 20 and a new abutment 30 and/or dental prosthetic may be inserted to replace the damaged abutment 30.

A medium (not shown) may also be inserted into the aperture 60 to improve the pressure build-up within the chamber 26. The medium for removal of the abutment 30 must be of sufficient viscosity, such as would be known to those skilled in the art of hydrostatics or hydrodynamics. In some embodiments, the medium may have the consistency of peanut butter. A thicker medium may also be beneficial as splashing may be reduced. In addition, a thicker medium has a reduced chance of being swallowed by a patient and a thicker medium may be easier for a dentist or dental surgeon to work with inside a patient's mouth. In a preferred embodiment, the medium may be medical grade glycerol and have a viscosity of about 1.425 Pascal. Furthermore, the medium may be flavoured or non-flavoured. It should be understood that other mediums are possible. For example, water and/or saline may be used.

In a preferred embodiment, a hydraulic pump (not shown) may be used to provide the predetermined amount of hydraulic pressure necessary to eject the insertion portion 50 from the cavity 22. A suitable attachment mechanism may be connected to the hydraulic pump to create a seal around the attachment opening 62 of the aperture 60. For example, a hydraulic pump with an elastomer seal (i.e. a gasket) or probe may be inserted into the attachment opening 62. In this manner, the hydraulic pressure within the chamber 26 may be increased until the predetermined amount of hydraulic pressure is achieved and the insertion portion 50 is ejected from the cavity 22.

In an alternate embodiment, a piston or other suitable device such as a pin or shaft (not shown) may be used to generate the necessary predetermined amount of hydraulic pressure. If the aperture 60 is cylindrical, the pin may be constructed with a diameter slightly smaller than the diameter d of the aperture 60. For example, the pin may have a diameter 0.0005 of an inch smaller than the diameter d of the aperture 60. Thus, when the pin is placed into the aperture 60, the pin may act as a micro hydraulic pump. When the pin is inserted further into the aperture 60 towards the insertion opening 64, pressure builds up within the chamber 26 between the insertion portion 50 and the cavity 22. When the build-up of pressure exceeds the predetermined amount of hydraulic pressure, the taper lock between the abutment sidewall 52 and the cavity sidewall 24 is overcome and the insertion portion 50 is ejected from the cavity 22.

Figure 5:
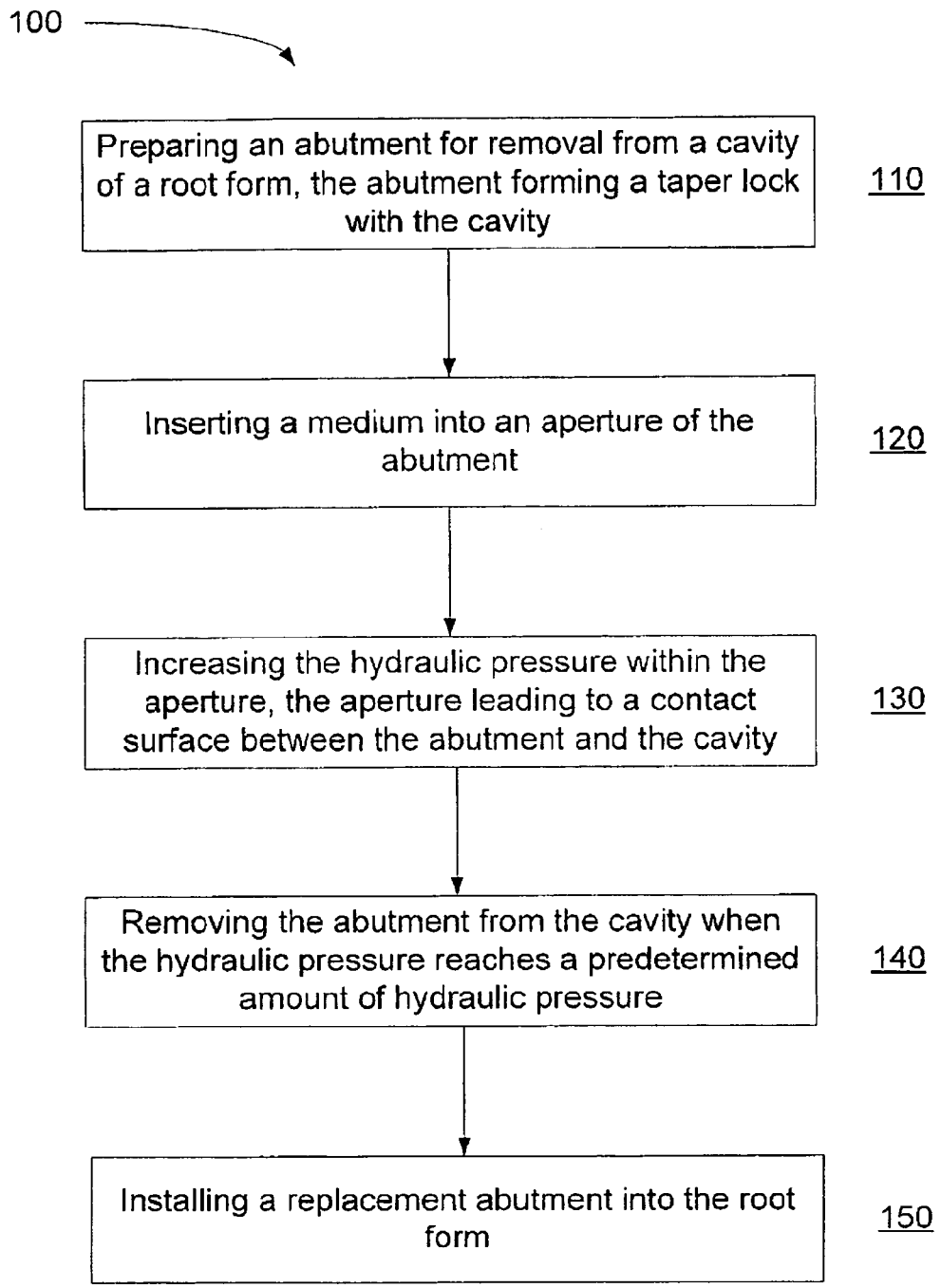
FIG. 5 shows a flow chart to remove an abutment from the root form in accordance with an embodiment of the present invention.

Reference is now made to FIG. 5 showing a flow chart 100 to remove an abutment 30 from the root form 20 in accordance with an embodiment of the present invention. In BLOCK 110, the method begins by preparing the abutment 30 for removal from the cavity 22. As a dental prosthesis may be connected to the attachment portion 40, this may involve removing the dental prosthesis to gain access to the attachment opening 62 of the aperture 60. If a prosthetic fastener 12 is used, the prosthetic fastener 12 may also be removed. For example, the prosthetic fastener 12 may be uncoupled from the abutment 30 by unscrewing the prosthetic fastener 12 from the attachment opening 62.

In BLOCK 120, a medium (not shown) is inserted into the aperture 60. For example, the medium may have the consistency as thin as olive oil to as thick as toothpaste or thicker.

In a preferred embodiment, medical grade glycerol is used. The inventor has appreciated that it is more practical to use a thicker medium with a hydraulic pump. The medium may improve the fluid dynamics of increasing and distributing the pressure between the insertion portion 50 and the cavity 22. Furthermore, the medium may aid in overcoming the taper lock between the abutment sidewall 52 and the cavity sidewall 24.

In BLOCK 130, the hydraulic pressure within the aperture 60 is increased. As mentioned, the aperture 60 leads to the chamber 26 formed between the insertion portion 50 and the cavity 22. The hydraulic pressure is increased until a predetermined amount of hydraulic pressure is achieved such that the taper lock between the abutment 30 and the root form 20 is overcome.

In some embodiments, a hydraulic pump may be used. In such a situation, the pressure may be increased gradually until the taper lock is overcome. In other embodiments, a pin or shaft may be inserted into the aperture 60 to generate the predetermined amount of hydraulic pressure. In such a situation, the shaft may be quickly pressed or jerked into the aperture 60 to create the necessary pressure. In other situations, a small mallet or light hammer may be used to generate the necessary predetermined amount of hydraulic pressure.

In BLOCK 140, the abutment 30 is removed from the cavity 22 when the abutment 30 has been ejected from the cavity 22 and the taper lock has been overcome by the predetermined amount of hydraulic pressure. The predetermined amount of hydraulic pressure required to separate the insertion portion 50 from the cavity 22 is based on the design and configuration of the dental implant system 10. For example, based on the shape and finish of the insertion portion 50 and the cavity 22, the predetermined amount of hydraulic pressure may be greater than 1500 psi. Furthermore, the predetermined amount of hydraulic pressure may be as high as 9500 psi, or greater. In preferred embodiments, the predetermined amount of hydraulic pressure may be between 2000 psi and 4000 psi and more preferably between 2500 psi and 3500 psi. The amount of hydraulic pressure may rise as high as 9700 psi. The amount of the hydraulic pressure will depend upon the formula used to determine the rate of taper on the abutment. There is a direct correlation between the degree of taper and the release pressure. The amount of hydraulic pressure required can be achieved by changing the incline of the taper.

Finally, in BLOCK 150, a replacement abutment is installed into the root form 20. The replacement abutment may correct the damage to the dental prosthetic, for example, suffered during a trauma. Assuming the root form 20 has not been damaged, the replacement abutment is operable to form a new taper lock with the root form 20. In this manner, the present invention does not require the surgical removal of a previous root form prior to the installation of a replacement abutment.

Although this disclosure has described and illustrated certain preferred embodiments of the invention, it is also to be understood that the invention is not restricted to these particular embodiments rather, the invention includes all embodiments which are functional, or mechanical equivalents of the specific embodiments and features that have been described and illustrated herein. The scope of the claims should not be limited by the preferred embodiments set forth in the examples, but should be given the broadest interpretation consistent with the description as a whole.

It will be understood that, although various features of the invention have been described with respect to one or another of the embodiments of the invention, the various features and embodiments of the invention may be combined or used in conjunction with other features and embodiments of the invention as described and illustrated herein.

The embodiments of the invention in which an exclusive property or privilege is claimed is defined as follows:

1. A dental implant system comprising:
   a root form for attaching to a patient's jaw bone, the root form having a cavity; and
   an abutment having an attachment portion, an insertion portion and an aperture, the insertion portion receivable within said cavity and forming a taper lock therein and the aperture passing through the abutment from the attachment portion to the insertion portion,
   wherein the aperture is configured to receive a predetermined amount of hydraulic pressure to eject the abutment from the cavity, whereby the predetermined amount of hydraulic pressure is required to overcome the taper lock between the insertion portion of fine abutment and the cavity
   wherein the system further comprises a means for generating the predetermined amount of hydraulic pressure to said aperture.

2. The dental implant system of claim 1, wherein when the abutment is received within the cavity, a chamber is formed in the cavity between the cavity and the insertion portion of the abutment.

3. The dental implant system of claim 2, wherein the insertion portion of the abutment is frustoconical.

4. The dental implant system of claim 1, wherein the insertion portion of the abutment is frustoconical.

5. The dental implant system of claim 1, wherein the means for generating the predetermined amount of hydraulic pressure in said aperture is a piston for insertion into the aperture to generate the predetermined amount of hydraulic pressure.

6. The dental implant system of claim 1, wherein the predetermined amount of hydraulic pressure is greater than 1500 psi.

7. The dental implant system of claim 1, wherein the predetermined amount of hydraulic pressure is between 2000 psi and 4000 psi.

8. The dental implant system of claim 1, wherein the predetermined amount of hydraulic pressure is between 1500 psi and 9700 psi.

9. The dental implant system of claim 1, wherein the means for generating the predetermined amount of hydraulic pressure in said aperture is a hydraulic pump to generate the predetermined amount of hydraulic pressure.

10. A dental implant system comprising:
   a root form for attaching to a patient's jaw bone, the root form having a cavity;
   an abutment having an attachment portion, an insertion portion and an aperture, the insertion portion receivable within said cavity and forming a taper lock therein and the aperture passing through the abutment from the attachment portion to the insertion portion,
   wherein the aperture is configured to receive a predetermined amount of hydraulic pressure to eject the abutment from the cavity, whereby the predetermined amount of hydraulic pressure overcomes the taper lock between the insertion portion of the abutment and the cavity; and
   a piston for insertion into the aperture to generate the predetermined amount of hydraulic pressure.

11. The dental implant system of claim 10, wherein the predetermined amount of hydraulic pressure is greater than 1500 psi.

12. The dental implant system of claim 10, wherein the predetermined amount of hydraulic pressure is between 2000 psi and 4000 psi.

13. The dental implant system of claim 10, wherein the predetermined amount of hydraulic pressure is between 1500 psi and 9700 psi.

14. A dental implant system comprising:
   a root form for attaching to a patient's jaw bone, the root form having a cavity;
   an abutment having an attachment portion, an insertion portion and an aperture, the insertion portion receivable within said cavity and forming a taper lock therein and the aperture passing through the abutment from the attachment portion to the insertion portion,
   wherein the aperture is configured to receive a predetermined amount of hydraulic pressure to eject the abutment from the cavity, whereby the predetermined amount of hydraulic pressure overcomes the taper lock between the insertion portion of the abutment and the cavity; and
   a hydraulic pump to generate the predetermined amount of hydraulic pressure.

15. The dental implant system of claim 14, wherein the predetermined amount of hydraulic pressure is greater than 1500 psi.

16. The dental implant system of claim 14, wherein the predetermined amount of hydraulic pressure is between 2000 psi and 4000 psi.

17. The dental implant system of claim 14, wherein the predetermined amount of hydraulic pressure is between 1500 psi and 9700 psi.

18. The dental implant system of claim 14, further comprising a medium for insertion into the aperture to improve pressure build-up between the insertion portion of the abutment and the cavity.

* * * * *